(12) United States Patent
    Li

(10) Patent No.: US 12,201,376 B2
(45) Date of Patent: Jan. 21, 2025

(54) ACCURATE POSITION DETERMINING DEVICE, METHOD AND SYSTEM FOR SURGICAL TOOL

(71) Applicant: BEIJING HURWA ROBOT MEDICAL TECHNOLOGY CO. LTD, Beijing (CN)

(72) Inventor: Shugang Li, Beijing (CN)

(73) Assignee: BEIJING HURWA ROBOT MEDICAL TECHNOLOGY CO.LTD, Shugang (LI)

( * ) Notice: Subject to any disclaimer, the term of this patent is extended or adjusted under 35 U.S.C. 154(b) by 511 days.

(21) Appl. No.: 17/489,156

(22) Filed: Sep. 29, 2021

(65) Prior Publication Data
US 2022/0022970 A1 Jan. 27, 2022

Related U.S. Application Data

(63) Continuation of application No. PCT/CN2021/089231, filed on Apr. 23, 2021.

(30) Foreign Application Priority Data

Jul. 1, 2020 (CN) .......................... 202010627367.1

(51) Int. Cl.
    A61B 34/20 (2016.01)
    A61B 34/30 (2016.01)
(52) U.S. Cl.
    CPC .............. *A61B 34/20* (2016.02); *A61B 34/30* (2016.02); *A61B 2034/2055* (2016.02)
(58) Field of Classification Search
    CPC .................... A61B 17/14; A61B 17/16; A61B 2017/00119; A61B 2017/00725;
    (Continued)

(56) References Cited

U.S. PATENT DOCUMENTS

2002/0016599 A1  2/2002  Kienzle, III et al.
2003/0209096 A1  11/2003 Pandey et al.
                 (Continued)

FOREIGN PATENT DOCUMENTS

CN    1511249 A     7/2004
CN    102608969 A   7/2012
              (Continued)

OTHER PUBLICATIONS

International Search Report dated Jul. 23, 2021 for International Patent Application No. PCT/CN2021/089231.
(Continued)

*Primary Examiner* — Andre J Allen

(57) ABSTRACT

The disclosure discloses an accurate position determining device, method and system for surgical tool. The method adopts two trackers for navigation and position determining: an end tracker is used for accurate position determining; the end tracker is removed after it is in place, and a main body tracker is used for real-time monitoring. Robotic arm movement will generate errors, and a navigation device is used to achieve multiple calibrations and successive recursion to approach a precise position, which thereby ensures a high accuracy to the utmost extent. During a navigation and position determining process, the main body tracker can provide a distance from a real-time position of a surgical tool to a spatial pose of a target cutting plane and feed it to an operator through a screen of a host, who makes fine adjustments by visual indication, and stops swinging if it exceeds a threshold value.

20 Claims, 13 Drawing Sheets

(58) Field of Classification Search
CPC .... A61B 2034/2055; A61B 2090/3937; A61B 2090/3983; A61B 34/20; A61B 34/30
See application file for complete search history.

(56) References Cited

U.S. PATENT DOCUMENTS

| | | | |
|---|---|---|---|
| 2004/0034300 A1 | 2/2004 | Verard | |
| 2014/0088410 A1 | 3/2014 | Wu | |
| 2015/0100066 A1* | 4/2015 | Kostrzewski | A61B 34/30 606/130 |
| 2016/0235483 A1 | 8/2016 | Zeilhofer et al. | |
| 2016/0278864 A1 | 9/2016 | Paitel | |
| 2016/0278875 A1 | 9/2016 | Crawford | |
| 2017/0143429 A1 | 5/2017 | Richmond et al. | |
| 2017/0252109 A1 | 9/2017 | Yang et al. | |
| 2019/0274775 A1 | 9/2019 | Olive | |
| 2020/0008889 A1 | 1/2020 | Ho | |
| 2020/0121400 A1 | 4/2020 | Girardeau-Montaut | |
| 2020/0375670 A1* | 12/2020 | Bonny | A61B 34/20 |
| 2023/0146679 A1* | 5/2023 | Lavallee et al. | A61B 34/20 700/259 |
| 2023/0248470 A1* | 8/2023 | Crawford | B25J 13/089 600/473 |
| 2024/0138932 A1* | 5/2024 | Riding | A61B 17/1728 |

FOREIGN PATENT DOCUMENTS

| | | | |
|---|---|---|---|
| CN | 103705307 A | 4/2014 | |
| CN | 104260095 A | 1/2015 | |
| CN | 104688322 A | 6/2015 | |
| CN | 105813592 A | 7/2016 | |
| CN | 205649543 U | 10/2016 | |
| CN | 205729508 U | 11/2016 | |
| CN | 106308940 A | 1/2017 | |
| CN | 108309450 A | 7/2018 | |
| CN | 108938090 A | 12/2018 | |
| CN | 108969100 A | 12/2018 | |
| CN | 109303596 A | 2/2019 | |
| CN | 109591019 A | 4/2019 | |
| CN | 109864806 A | 6/2019 | |
| CN | 208974099 U | 6/2019 | |
| CN | 110215284 A | 9/2019 | |
| CN | 110652360 A | 1/2020 | |
| CN | 111000632 A | 4/2020 | |
| CN | 111012503 A | 4/2020 | |
| CN | 111095425 A | 5/2020 | |
| CN | 111317572 A | 6/2020 | |
| EP | 3 409 231 A1 | 12/2018 | |
| IN | 208808648 U | 5/2019 | |
| IN | 111956325 A | 11/2020 | |
| JP | 2017-205495 A | 11/2017 | |
| JP | 2020-96833 A | 6/2020 | |
| KR | 10-2017-0125023 A | 11/2017 | |
| WO | 2013189520 A1 | 12/2013 | |
| WO | 2018/102926 A1 | 6/2018 | |
| WO | 2018/220050 A1 | 12/2018 | |
| WO | 2020/072335 A1 | 4/2020 | |
| WO | WO-2020186194 A1* | 9/2020 | A61B 34/10 |

OTHER PUBLICATIONS

The Notice of Reasons for Refusal for Japanese Patent Application No. 2021-568024, dated Oct. 25, 2022.
The First Office Action for Chinese Patent Application No. 202110838716.9, dated Dec. 21, 2022.
The Extended European Search Report for European Patent Application No. 21765820.2, dated Jun. 7, 2022.
The Notice of Registration for Chinese Patent Application No. 202110838716.9, dated Jul. 25, 2023.
The Request for the Submission of an Opinion for Korean Patent Application No. 10-2021-7036511, dated Sep. 15, 2023.
Decision to Grant a Patent dated Sep. 26, 2024 for Korean Patent Application No. 10-2021-7036511.

* cited by examiner

ACCURATE POSITION DETERMINING DEVICE, METHOD AND SYSTEM FOR SURGICAL TOOL

CROSS-REFERENCE TO RELATED APPLICATION

This application is a continuation of International Application No. PCT/CN2021/089231, filed on Apr. 23, 2021, which claims priority to Chinese Patent Application No. 202010627367.1, filed on Jul. 1, 2020, both of which are incorporated herein by reference in their entireties.

FIELD

The disclosure relates to a technical field of computer-assisted surgery, and in particular to a computer-assisted surgical navigation system using a collaborative robotic arm, and a device, a method, and a system for accurately determining a position of a surgical tool in a surgical navigation system.

BACKGROUND

With development of computer technology, computer-assisted surgery systems are also developing rapidly. In such systems, in order to facilitate operations such as movement, a collaborative robotic arm is usually provided. A main difference between a collaborative robotic arm and other types of robotic arm is that when a collaborative robotic arm is used, a human hand can hold the collaborative robotic arm in its operation process to directly manipulate the robotic arm by pushing, pulling, lifting, pressing and the like; by using the collaborative robotic arm, it is possible to provide more flexible control modes for an end effector or a surgical tool and provide better adaptability for complex scenarios. Unlike a fixed movement trajectory of a traditional robotic arm, the collaborative robotic arm is more unpredictable in respect of its movement path since it can be operated with the assistance of human hands, which thereby has higher real-time and more accurate requirements for determining the position of the end effector or the surgical tool.

A distal end of the collaborative robotic arm is usually equipped with an end effector, and a distal end of the end effector will be equipped with different surgical tools according to different scenarios, such as saws, drills, milling cutters, etc. (in the disclosure, a "proximal end" refers to an end relatively closer to a robotic arm operator and farther away from a patient, and a "distal end" refers to an end relatively farther away from the robotic arm operator and closer to the patient). Through mechanical connection mechanisms and control operations between the collaborative robotic arm, the end effector, and the surgical tool, cutting, drilling, grinding and other actions on targets are realized. In order to ensure accurate operation, it is very important that most distal positions (also called front end or end) of the end effector, especially the surgical tool is accurately positioned. Only by determining the end position of the surgical tool as accurately as possible, the system can accurately determine a relationship of the end position of the surgical tool and a target position, so as to ensure that the surgical tool moves accurately to the target position and can accurately move according to a predetermined spatial trajectory movement and complete the operations.

In prior art, determining of the end position of the surgical instrument is usually performed by a method of tracking an optical tracker with an optical navigator. In other words, an optical tracker with a tracking marker is mounted on an object to be positioned or tracked, and an optical navigator tracks the tracking marker on the tracker to determine a position of the tracker and thus a position of the object to be tracked. For example, a patent published as CN111012503A and entitled "Surgical Robot Automation With Tracking Marker" discloses a method for automating a surgical robot by using a tracking marker, and discloses that the tracking marker includes a conventional reflective ball which can be tracked by a commercially available optical tracking system, the optical tracker with the tracking marker is mounted on a surgical device (e.g., screwdriver, dilator, implant inserter, etc.), and the tracking marker enables each of the marked objects (e.g., end effector 112, patient 210, and surgical tool 608) to be tracked by a robot 102.

However, there are certain problems with the above method. First, generally speaking, because surgical tools are used for specific surgical operations, they usually have a small size and shall be ensured to have a certain movement space and a certain degree of freedom; an electric saw, which is taken as an example, is one of surgical tools commonly carried by the end effector and can cut targets efficiently and is suitable for such as total knee replacement surgery and the like. When a tracking and position-determining method in prior art is applied to a high-speed swinging surgical tool such as an electric saw, because the electric saw blade has been swinging at a high speed during the surgery (the swinging speed of the saw blade is up to 8800 times/min), it is difficult to fix the optical tracker; and the mounting of the optical tracker on the saw blade will inevitably affect a field of view and an operating space during the surgery, and accordingly will also affect the operations during the surgery. Furthermore, during the surgical operation, it is easy to contaminate the tracking marker on the optical tracker fixed on the saw blade by accidental touching and so on, which affects the position-determining and tracking effect. More importantly, since existing optical tracking instruments can only reach a maximum sampling frequency of 60 frames per second while the swinging speed of the saw blade is as high as 8800 times/minute, the mounting of the tracker on the saw blade swinging at a high-speed also means that the optical navigator cannot accurately capture an actual exact position of the saw blade.

However, in practice, the end position of the saw blade needs to be accurately positioned to ensure that it moves in a predetermined trajectory to perform the cutting operation. As mentioned above, it is almost impossible to mount the tracker on the surgical tool, especially the saw blade, and possible options include mounting the optical tracker at a distance from the saw blade that does not affect the surgical operation, such as near a flange at the end of the robotic arm or on the end effector, and converting position information obtained based on the optical tracker to position information of the end of the surgical tool according to relation of mechanical structures. However, the accuracy of this solution is unreliable for the following reasons: first, physical relationship of the end of the surgical tool and the tracker need to be guaranteed by mechanical processing, which will produce errors; second, there are multiple assembly steps when the surgical tool is assembled to the end effector, which will produce errors; third, the optical navigator when acquiring the spatial coordinate position of the optical tracker will also produce errors, and at a same angle, the farther the distance, the greater the error, thus the distance between the tracker and the end also magnifies the optical error. Therefore, there is a need for a solution that can improve the accurate position-determining of the end position of the surgical tool to solve the above problems in prior art.

SUMMARY

To solve the problem in prior art that a surgical tool need to be accurately positioned, the disclosure provides an accurate position determining device for a surgical tool, an accurate position determining method for a surgical tool and an accurate position determining system for a surgical tool. The position determining device, the position determining method and the position determining system can significantly improve a position determining accuracy of the surgical tool, especially at an end position of the surgical tool.

The disclosure provides a surgical tool accurate position determining device for accurately determining an end position of a surgical tool, the position determining device including: an optical navigation device and a robotic arm device, wherein an end effector is connected to an end of the robotic arm device, a main body tracker is disposed at a main body of the end effector, a surgical tool is disposed at an end of the end effector, an end tracker is disposed at the surgical tool, and the end tracker is detachably connected to the surgical tool.

In any embodiment of the disclosure, the position determining device including: an optical navigation device and a robotic arm device, an end effector is connected to an end of the robotic arm device, the end effector includes a main body portion, a handle end, an output end and a tracker end extend from the main body portion, the main body tracker is disposed at the tracker end, a surgical tool is disposed at the output end, an end tracker is disposed at the surgical tool, and the end tracker is detachably connected to an end of the surgical tool.

In any embodiment of the disclosure, the end tracker includes a tracker main body, a slot, a locking mechanism and a plurality of reflective balls, wherein the slot and the locking mechanism are located on one side face of the tracker main body, the reflective balls are located on the other side face of the tracker main body.

In any embodiment of the disclosure, the locking mechanism is located on one side wall forming the slot, the slot is adapted to be inserted by the surgical tool and to snap-fittingly fix the surgical tool by means of the locking mechanism.

In any embodiment of the disclosure, the locking mechanism includes a resilient ball mechanism for providing an elastic force for fixing the surgical tool against the other side wall of the slot.

In any embodiment of the disclosure, the resilient ball mechanism includes an accommodating tube, a spring and a resilient ball. In some embodiments, the side wall of the slot on which the locking mechanism is disposed includes a through hole, the accommodating tube is fixed in the through hole, one end of the spring is fixed at a bottom portion of the accommodating tube, and the other end of the spring is connected to the resilient ball.

In any embodiment of the disclosure, an end reflecting ball is disposed at a vertex portion of the other side face of the end tracker main body, and the end reflecting ball is located close to the end of the surgical tool when the end tracker is snap-fittingly fixed to the surgical tool.

In any embodiment of the disclosure, the surgical tool is an electric saw blade that can swing at a high speed.

The disclosure also provides a surgical tool accurate position determining method, including a position predetermining phase and a navigating and position determining phase, wherein in the position predetermining phase, an optical navigation device is used to track a first position determining device to determine a position of an end of a surgical tool; and in the navigating and position determining phase, the optical navigation device is used to track a second position determining device to determine the position of the end of the surgical tool. Preferably, the first position determining device is an end tracker mounted at the end of the surgical tool; and the second position determining device is a main body tracker mounted at an end effector.

In any embodiment of the disclosure, in the position predetermining phase, the optical navigation device tracks a position of the end tracker, calculates a position relationship of the end tracker and a plane to be cut, and controls a movement of a robotic arm device.

In any embodiment of the disclosure, before the optical navigation device tracks the position of the end tracker, the method further includes a step of assembling the surgical tool and bringing it close to an initial position, and mounting the end tracker.

In any embodiment of the disclosure, a control instruction for controlling the movement of the robotic arm device is generated based on the calculated position relationship of the end tracker and the plane to be cut.

In any embodiment of the disclosure, after the robotic arm device has moved according to the instruction, the method further includes a step of updating and calculating position information of the end tracker.

In any embodiment of the disclosure, the step of updating and calculating the position information of the end tracker includes a step of updating tracking position information of the end tracker and a step of updating and calculating the position relationship of the end tracker and the plane to be cut.

In any embodiment of the disclosure, the method further includes: a step of determining whether a distance between the end tracker and the plane to be cut exceeds a threshold range, in which step, if the distance exceeds the threshold range, a control instruction is generated and sent to a control unit according to the updated and calculated position relationship to control the robotic arm device to move according to the instruction.

In any embodiment of the disclosure, after the position predetermining phase is finished, the method further includes a step of recording and storing a position relationship of the end tracker and the main body tracker.

In any embodiment of the disclosure, in the navigating and position determining phase, the optical navigation device tracks a position of the main body tracker, calculates a position relationship of the end of the surgical tool and the plane to be cut, and controls the movement of the robotic arm device.

In any embodiment of the disclosure, before the navigating and position determining phase, the method further includes a step of calculating a position relationship of the end tracker and the main body tracker and a step of storing the position relationship as a first calibration parameter.

In any embodiment of the disclosure, the method further includes: a step of calculating a position relationship of the main body tracker and the plane to be cut according to the first calibration parameter, and a step of storing the position relationship as a second calibration parameter.

In any embodiment of the disclosure, during navigation, a real time position of the end of the surgical tool is calculated and obtained according to the second calibration parameter.

In any embodiment of the disclosure, the navigating and position determining phase includes following steps: a step of calculating and storing a position relationship of a coordinate system in which the main body tracker is located and a coordinate system in which the end tracker is located; a step of calculating and storing a position relationship of the coordinate system in which the main body tracker is located and a coordinate system in which a plane to be cut is located; a step of removing the end tracker, controlling the surgical tool to move according to a predetermined trajectory, and also tracking position information of the main body tracker; and a step of calculating, in real time, a distance between an end point position of the surgical tool and the plane to be cut according to the tracked position information of the main body tracker.

In any embodiment of the disclosure, the method further includes a step of determining whether the distance between the end point position of the surgical tool and the plane to be cut exceeds a threshold range. In some embodiments, an alarm is issued if it is determined that the distance deviates from the predetermined range.

In any embodiment of the disclosure, the method further includes a step of setting a resisting force parameter for the robotic arm device to limit a range of movement of a robotic arm.

In any embodiment of the disclosure, after the surgical tool has finished cutting operations at a plane to be cut, the surgical tool returns to an initial position and the end tracker is mounted, a position at which a next plane to be cut is located is set as a target cutting plane position, and the steps of the position predetermining phase and the navigating and position determining are further carried out.

The disclosure also provides a surgical tool accurate position determining system, which performs the surgical tool accurate position determining method provided in the disclosure.

In any embodiment of the disclosure, the system includes: a tracker information reading unit, including a unit for reading information of an end tracker which reads a coordinate system in which the end tracker is located from the optical navigation device, and a unit for reading information of a reference frame, which reads a coordinate system in which the reference frame is located from the optical navigation device; a position relationship calculating unit, for calculating a position relationship of the coordinate system in which the end tracker is located and a coordinate system in which a plane to be cut is located, based on the coordinate system in which the end tracker is located and the coordinate system in which the reference frame is located; an instruction generating unit for generating and sending a control instruction for controlling a movement of the robotic arm device based on the position relationship calculated by the position relationship calculating unit; a position relationship updating unit for updating and calculating the position relationship of the coordinate system in which the end tracker is located and the coordinate system in which the plane to be cut is located after the robotic arm device has moved; and a determining unit for determining whether the position relationship updated and calculated by the position relationship updating unit is less than a predetermined threshold value, generating and sending a control instruction to control the movement of the robotic arm device according to the updated and calculated position relationship if it is greater than the predetermined threshold value, and generating an instruction to stop the movement if it is less than the predetermined threshold value.

In any of the embodiments of the disclosure, the system further includes: a main body tracker information reading unit for reading from the optical navigation device position information of a coordinate system in which a main body tracker is located; a calibration parameter calculating unit for calculating a position relationship of the coordinate system in which the end tracker is located and the coordinate system in which the main body tracker is located based on the coordinate system in which the end tracker is located and the coordinate system in which the main body tracker is located; a position relationship calculating unit for calculating a position relationship of the coordinate system in which the main body tracker is located and the coordinate system in which the plane to be cut is located, based on the position information of the coordinate system in which the main body tracker is located, the position information of the coordinate system in which the reference frame is located, a calibration parameter, and known position relationship of the coordinate system in which the reference frame is located and the coordinate system in which the plane to be cut is located; a real-time calculating unit for calculating and obtaining a real-time position of the end of the surgical tool according to the position information of the coordinate system in which the main body tracker is located and the position relationship that are real-time obtained; and a deviation determining unit for calculating a distance between a plane position of the end of the surgical tool and the coordinate system in which the plane to be cut is located, and determining whether the distance deviates from a predetermined range.

In any embodiment of the disclosure, the surgical tool is a saw blade, and the resisting force along a direction perpendicular to a plane in which the saw blade is located is set to be $F=kx$, wherein a resisting force coefficient k is 4000-6000 N/mm, and x denotes a moving distance of the surgical tool. Preferably, k is 5000 N/mm.

The disclosure further provides a storage medium including a program stored thereon, wherein the method provided in the disclosure is performed when the program is executed.

The disclosure also provides a processor including a program stored thereon, wherein the method provided in the disclosure is performed when the program is executed.

The surgical tool accurate position determining device provided in the disclosure includes the end tracker which is precisely and detachably designed for the end of the surgical tool, so that the end tracker can be quickly and conveniently mounted on the end of the surgical tool; and after the end tracker is mounted, the end tracker is cooperated with the optical navigation device, which can achieve the accurate position determining of the end position of the surgical tool.

The surgical tool accurate position determining method provided in the disclosure includes at least the position predetermining phase and the navigating and position determining phase. In the position predetermining phase, the end tracker is cooperated with the optical navigation device, which can accurately track the end position of the surgical tool. According to the position relationship of the coordinate system in which the end tracker for the surgical tool is located and the coordinate system in which the target plane is located, the control instruction is generated for controlling the movement of the collaborative robotic arm along with the surgical tool, so that it can advance to the precise target position by successive approximation, which can ensure that it moves to the most precise position. In the navigating and position determining phase, the end tracker is removed, and the position relationship of the coordinate system in which the end tracker is located and the coordinate system in which the main body tracker is located, which is recorded at the end of the position predetermining phase, is used as the calibration parameter. During the movement of the surgical tool, the position information of the main body tracker is tracked, and the position of the end of the surgical tool is calculated in combination with the calibration parameter. In this way, the more accurate real-time position determining of the end position can be obtained, and during the movement of the surgical tool, it is determined in real time whether its end position deviates from the predetermined trajectory so as to timely take measures. The accurate position determining method provided in the disclosure is also applicable to the case of multiple target planes to be cut. After cutting operations in a target plane to be cut have been finished, the surgical tool returns to the initial position and performs the steps in the position predetermining phase and the navigating and position determining phase with respect to a next target plane to be cut, so as to ensure that it can be accurately positioned and navigated for each plane to be cut, until cutting operations in the target plane are finished.

The surgical tool accurate position determining system provided in the disclosure can use the surgical tool accurate position determining device to perform the surgical tool accurate position determining method, can accurately track the end position of the surgical tool in real time and ensure surgery reliability and safety.

BRIEF DESCRIPTION OF THE DRAWINGS

In order to more clearly illustrate technical solutions according to embodiments of the disclosure or in prior art, a brief description of accompanying drawings to be used in the description of the embodiments or prior art will be given below; it is obvious that the accompanying drawings in the following description are some embodiments of the disclosure, and other accompanying drawings can be obtained according to these accompanying drawings without any creative work for a person of ordinary skill in the art.

DETAILED DESCRIPTION

Figure 1:
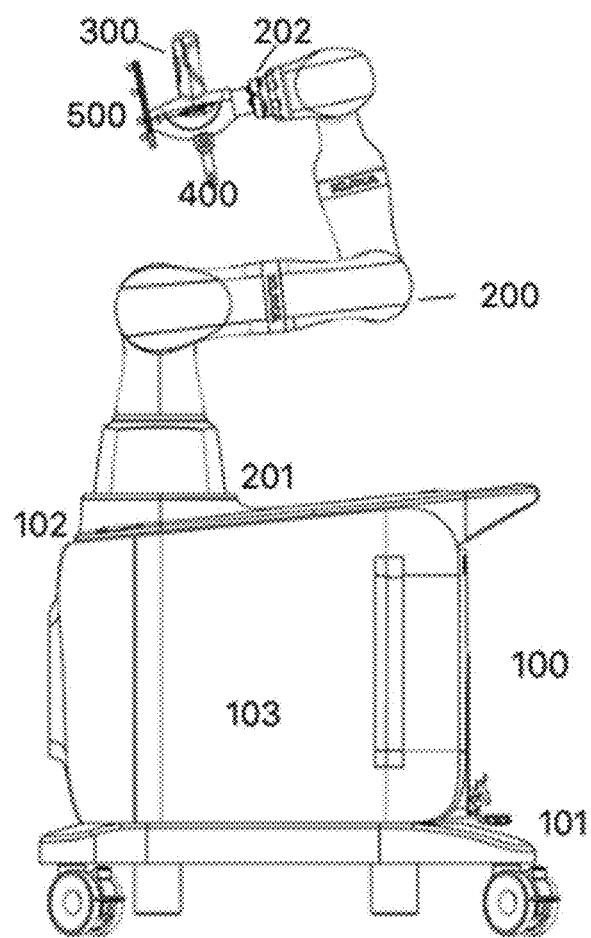
FIG. 1 is a structural schematic diagram of a robotic arm device in an embodiment of the disclosure.

In order to enable those skilled in the art to better understand solutions of the disclosure, technical solutions in embodiments of the disclosure will be described clearly and completely in conjunction with accompanying drawings in embodiments of the disclosure.

Some processes described in the specification, claims and the above accompanying drawings of the disclosure include a plurality of operations appearing in a specific order, but it should be clearly understood that these operations may be executed in parallel or executed in a different order from the order described in the disclosure, and that serial numbers of the operations are used only to distinguish various different operations and do not represent any order of execution. Alternatively, these processes may include more or fewer operations, and these operations may be performed sequentially or in parallel. It should be noted that the terms "first", "second", etc. in the disclosure are used to distinguish different messages, devices, modules, etc. and do not represent a sequential order or limit "first" and "second" to be different types.

References throughout the disclosure to "multiple embodiments", "some embodiments", "one embodiment" or "an embodiment", etc., mean that a specific feature, component or characteristic described in conjunction with the embodiment(s) is included in at least one embodiment. Therefore, phrases "in multiple embodiments", "in some embodiments", "in at least another embodiment" or "in an embodiment" appearing throughout the disclosure do not necessarily all refer to the same embodiment. Furthermore, in one or more embodiments, specific features, components, or characteristics may be combined in any suitable manner. Therefore, without limitation, the specific features, components or characteristics shown or described in conjunction with one embodiment may be combined in whole or in part with the features, components or characteristics of one or more other embodiments. Such modifications and variations are intended to be included within the scope of the disclosure.

Furthermore, those skilled in the art can understand that various aspects of the disclosure can be explained and described through a number of patentable categories or situations, including any new and useful process, machine, product, or substances, or a combination of them, and any new and useful improvements of them. Correspondingly, various aspects of the disclosure can be completely executed by hardware, can be completely executed by software (including firmware, resident software, microcode, etc.), or can be executed by a combination of hardware and software. The above hardware or software can be called "data block", "module", "engine", "terminal", "component" or "system". Furthermore, various aspects of the disclosure may be embodied as a computer product in one or more computer readable media, and the product includes computer readable program codes.

It should be noted that terms "include", "having" or any other variants thereof are intended to cover non-exclusive inclusion, so that an article or device including a series of elements not only includes those elements, but also includes other elements that are not explicitly listed, or also include elements inherent to the process, method, article, or equipment. If there are no more restrictions, an element defined by a phrase "including a . . . " does not exclude the existence of other identical elements in the process, method, article, or equipment that includes the element.

The disclosure provides a surgical tool accurate position determining device for a computer-assisted surgical system, and the computer-assisted surgical system includes a robotic arm device and an optical navigation device. The surgical tool referred to in the disclosure is an instrumental device that can be used in medicine and assist surgeons to complete an examination or surgical operation; and for example, it can be an electric saw and its saw blade used in total knee replacement surgery, but it, not limited to this, can also be a clamp, drill, milling cutter, screwdriver, dilator, implant inserter, etc.

FIG. 1 shows a robotic arm device, which includes a control cabinet 100, a collaborative robotic arm 200, an end effector 300, a surgical tool 400, and an optical tracker 500 mounted on a main body of the end effector 300.

A control unit 103 is disposed in the control cabinet 100, and the control unit 103 has signal processing capability and may include, but not limited to, a Central Processing Unit (CPU), a Network Processor (NP), a Digital Signal Processor (DSP), a Special Purpose Integrated Circuit (ASIC), a Field Programmable Gate Array (FPGA) or other programmable logic device, a discrete gate or transistor logic device, a discrete hardware component, or any other chip or device having data processing and control capabilities. Various methods, steps and logic block diagrams disclosed in embodiments of the disclosure can be implemented or performed.

The control unit 103 can be connected to a host portion (not shown) of the system through an interface portion 101 of the control cabinet 100 to enable communication with a system host. The control unit 103 can receive control signals from the system host and convert them into operation instructions for controlling movement of the collaborative robotic arm 200.

The collaborative robotic arm 200 can receive the instructions from the control unit 103 and move according to movement modes defined by the instructions, or an operator can apply an external force to the collaborative robotic arm to push, pull, lift, press, etc. it under a manual control of the operator.

A top end of the control cabinet 100 is a base portion 102, and the base portion 102 of the control cabinet 100 is fixedly connected to a base end 201 of the collaborative robotic arm 200. The collaborative robotic arm 200 is a multi-axis robotic arm with the base end 201 as its proximal end, which is fixedly mounted at the base portion 102 of the control cabinet 100. A distal end of the collaborative robotic arm 200 is a flange end 202. The collaborative robotic arm 200 can receive instructions from the control unit 103 to enable the flange end 202 to complete rotating, translating or other actions and move to a spatial position defined by the instructions according to the movement modes defined by the instructions.

The flange end 202 of the collaborative robotic arm 200 is fixedly connected to the end effector 300, and the end effector 300 carries at its end a surgical tool 400. As an example, the surgical tool 400 carried on the end effector 300 according to the embodiment is a saw blade of an electric saw. The saw blade is driven by a motor of the electric saw, and the saw blade can be kept in a high-speed swinging state during its working process. As an example, an optical tracker 500 may also be mounted on the main body of the end effector 300.

Figure 2:
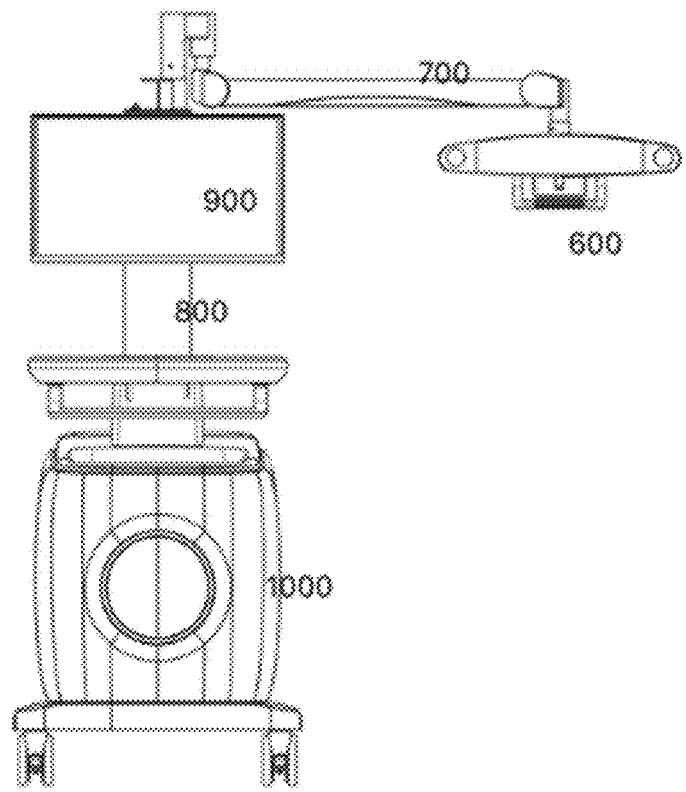
FIG. 2 is a structural schematic diagram of a host portion and an optical navigation device in an embodiment of the disclosure.

FIG. 2 shows the optical navigation device, and the system also includes a host portion 1000. The host portion can be a computer, or similar device with storage, computing, and communication functions. In FIG. 2, as an example, the optical navigation device is integrated with the system host 1000 in a single device; and it should understood that the optical navigation device and the system host can also be provided independently, or the system host can be integrated with the robotic arm device as shown in FIG. 1, as long as a secure connection and stable communication between the respective devices can be ensured.

The optical navigation device 600, as an example, may be a binocular navigation camera that tracks positions of tracking markers (usually respective reflective balls, but the tracking markers are not limited to this, as long as they are markers that can be tracked by the binocular navigation camera) on the optical tracker, thereby determining spatial pose information of the optical tracker.

In the embodiment shown in FIG. 2, the optical navigation device 600 is fixed to one end of a cantilever 700, and the other end of the cantilever 700 is fixed to a top portion of a column 800, a bottom portion of which is connected to a compartment portion housing the host 1000. Cables for data transmission, communication, and power supply pass through inner cavities of the column 800, the cantilever 700, and the compartment portion. The cantilever 700 is fixedly connected to the column 800 near the top portion in a way that the cantilever can be raised, lowered and rotated.

At a middle-upper portion of the column 800, a display unit 900 is also fixedly mounted. The display unit can be a liquid crystal display unit, a cathode ray tube display unit, a neon display unit, a vacuum fluorescent display unit, an electronic moving information display unit, a gas discharge display unit, a plasma display unit, or may adopt light emitting diode, electroluminescent material, fiber optic technology, laser technology, holographic technology, or any other technology for displaying information on the display unit. Furthermore, the display unit can display static or moving information, and the information can be displayed in different languages. It is advantageous to fix the display unit 900 at a height that allows the operator to easily watch it.

The host portion 1000 receives data from the optical navigation device 600, calculates a spatial relationship according to the method steps provided in the disclosure, generates movement control instructions, and sends the movement control instructions to the control unit 103 of the robotic arm device. The control unit 103 controls spatial movements of the collaborative robotic arm 200 according to the movement control instructions.

Figure 3:
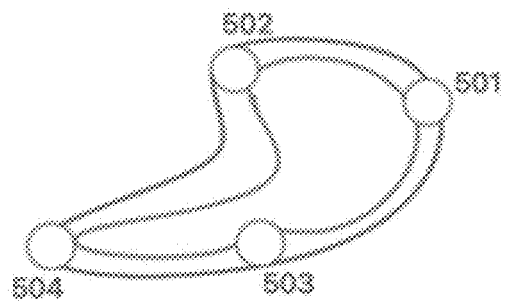
FIG. 3 is a structural schematic diagram of an optical tracker in an embodiment of the disclosure.

As an example of the optical tracker 500, a main body of the optical tracker 500 has a flat plate structure, as shown in FIG. 3. In some embodiments, the main body has a substantially crescent-shaped outer contour. Three or more reflective balls for tracking are disposed at intervals along an edge of the main body. As a preferred example, four reflective balls 501, 502, 503, 504 are disposed at approximately uniform intervals along the edge of the main body of the tracker. Each reflective ball is provided with a coating on its surface, and the coating can efficiently reflect infrared light.

Figure 4:
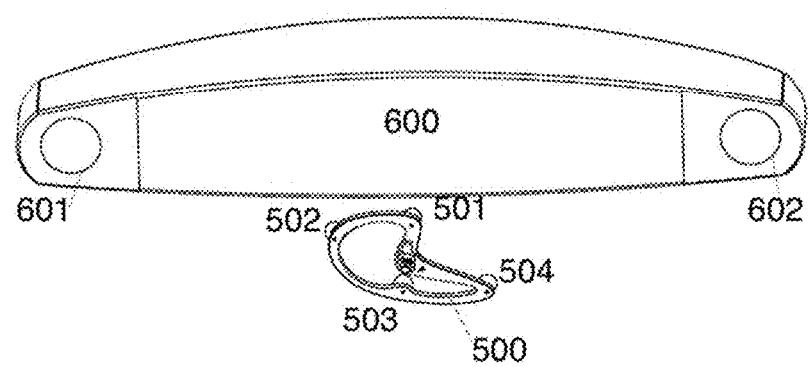
FIG. 4 is a structural schematic diagram of an optical navigation device in an embodiment of the disclosure.

As an example of the optical navigation device 600, as shown in FIG. 4, the optical navigation device 600 includes binocular cameras 601, 602. An infrared light emitter (not shown) is also integrated inside the optical navigation device 600. The infrared light emitter actively and outwardly emits infrared light, and the emitted infrared light is reflected by the reflective balls after irradiating the four reflective balls on the tracker 500 and is captured by the binocular cameras; the optical navigation device 600 can calculate the spatial pose information of the optical tracker 500 by a triangulation principle.

Figure 5:
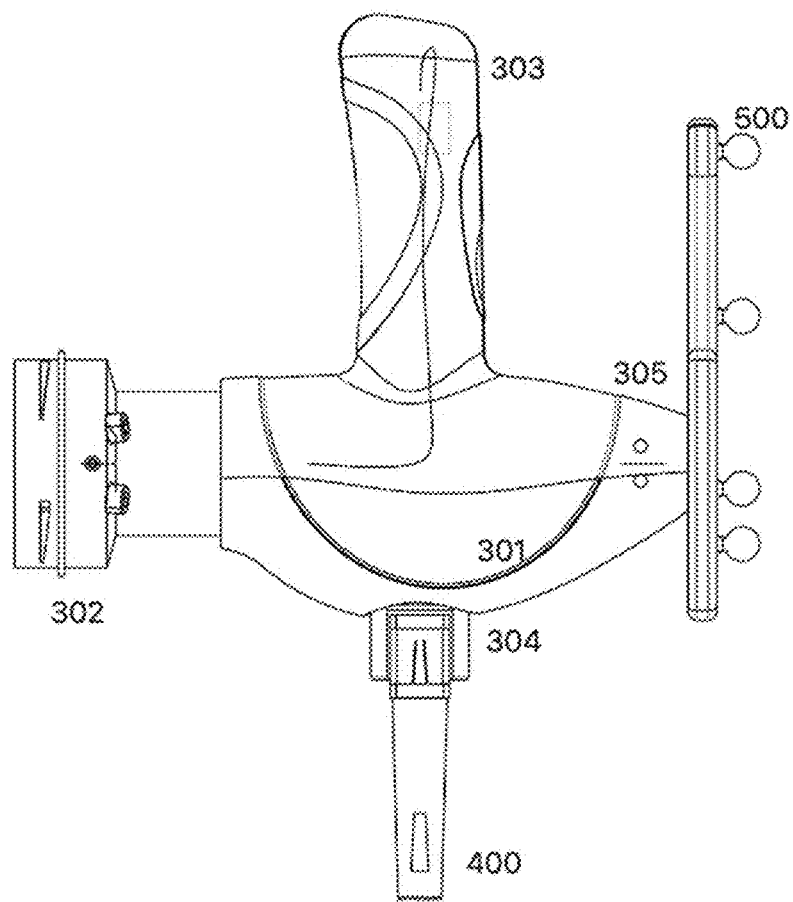
FIG. 5 is a structural schematic diagram of an end effector in an embodiment of the disclosure.

As an example of the end effector 300, as shown in FIG. 5, the end effector 300 includes a main body portion 301 from which a flange interface end 302 extends in one direction, and the flange interface end 302 is fixedly connected to a flange end 202 of the collaborative robotic arm 200 as described above.

On the main body portion, a tracker end 305 extends in another direction opposite to that of the flange interface end 302. The optical tracker 500 is fixedly mounted at the tracker end 305, hereinafter referred to as "main body tracker", which indicates that the tracker is mounted on the main body portion of the end effector, and a coordinate system in which the main body tracker is located is marked as $C_F$.

On the main body portion, a handle end 303 and an output end 304 extend, from two sides, in respective directions substantially perpendicular to the direction in which the flange interface end 302 extends. The handle end 303 can be held by an operator so that the operator can directly apply a force to the collaborative robotic arm to manipulate the movements of the robotic arm, the end effector and the surgical tool. The output end 304 serves as a mounting portion for surgical tools. As an example, an electric saw blade 400 is mounted on the output end 304, and the saw blade 400 is fixed by a pluggable snap-fit connection. When the electric saw is operating, the motor (not shown) of the electric saw located in the inner cavity of the main body portion 301 of the end effector drives the saw blade 400 to move according to a predetermined trajectory. During its movement according to the predetermined trajectory, the saw blade 400 also maintains a high-speed swinging action within a certain range in a horizontal direction in which the sheet-shaped main body is located.

Figure 6:
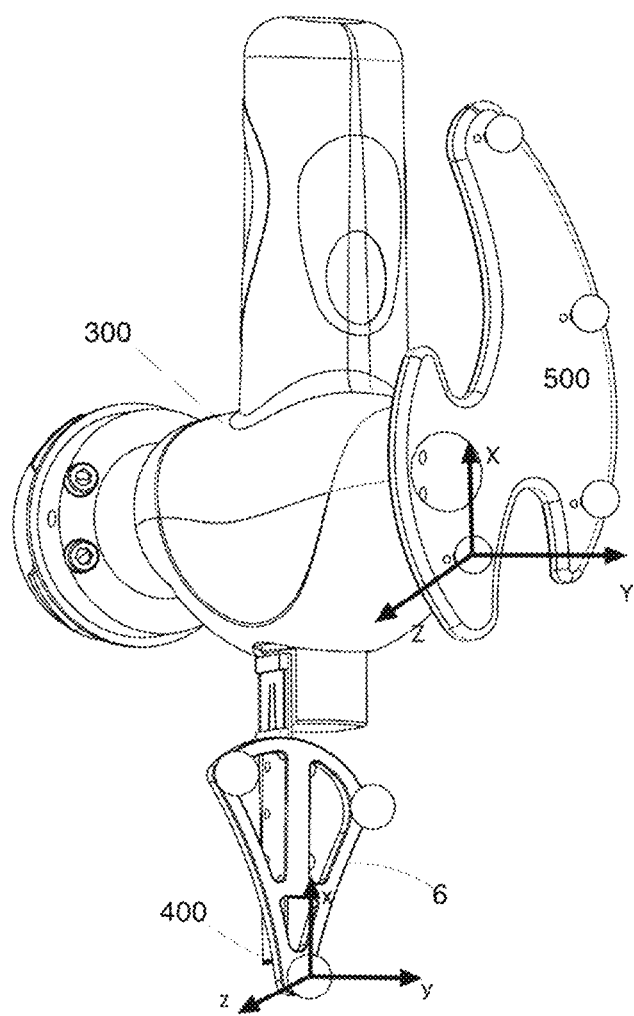
FIG. 6 is a structural schematic diagram of an end tracker mounted on an end effector in an embodiment of the disclosure.

In order to solve the problems described in the Background Section, the disclosure provides a tracker 6 for an end of a saw blade, hereinafter referred to as end tracker 6. FIG. 6 shows a position relationship of the end tracker 6 and the end effector 300; and as can be seen in FIG. 6, the main body tracker 500 is fixedly mounted at the tracker end 305 of the end effector 300, a coordinate system represented by the main body tracker is $C_F$. The saw blade 400 is fixedly mounted at the output end 304 of the end effector 300, and the end tracker 6 is mounted at or near the end of the saw blade 400, and a coordinate system represented by the end tracker is $C_V$.

Figure 7:
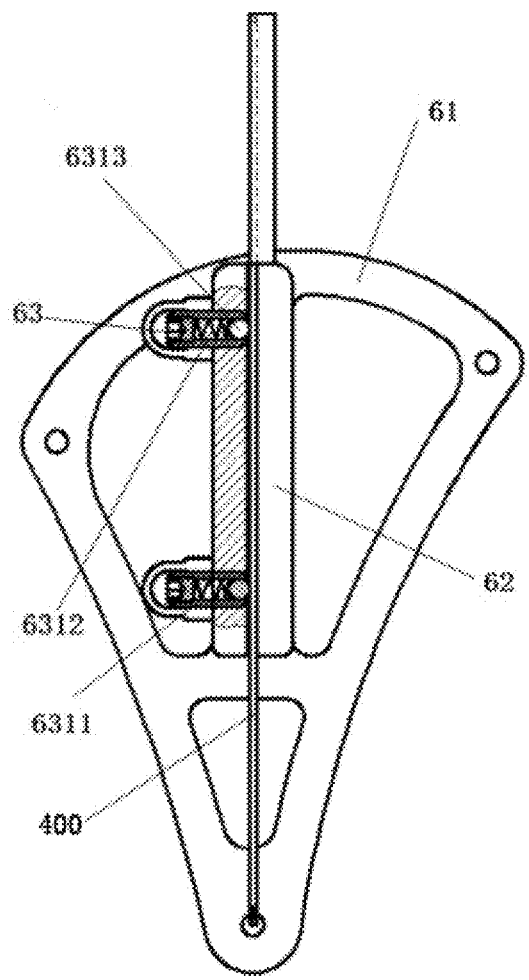
FIG. 7 is a structural schematic diagram of an end tracker in an embodiment of the disclosure.
Figure 8:
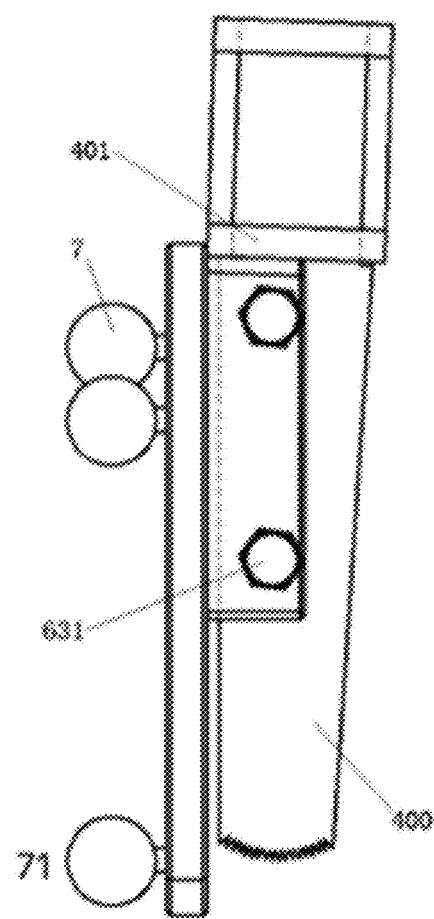
FIG. 8 is a side view of an end tracker in an embodiment of the disclosure.

As examples, FIGS. 7 and 8 show detailed structures of the end tracker 6, wherein FIG. 7 is a front view of the end tracker and FIG. 8 is a side view of the end tracker. The end tracker 6 is designed according to end characteristics of surgical tools (usually having a small size), and the end tracker includes a tracker main body 61, a slot 62, a locking mechanism 63, and a plurality of reflective balls 7. By means of the slot 62 and the locking mechanism 63, the end tracker main body can be easily fixed to an end of a surgical tool in a snap-fitting manner. The optical navigation device can track positions of the reflective balls 7 for establishing a coordinate system $C_V$ of the end tracker.

The tracker main body 61 is flat and has a generally inverted triangular shape with rounded edges. The slot 62 and the locking mechanism 63 are located on one side face of the tracker main body 61, and the reflective balls 7 are located on the other side face of the tracker main body 61. The number of the reflective balls can be set to 3 to 5. As an example, the embodiment provides 3 reflective balls, which are disposed near three vertex positions of the substantially triangular tracker main body 61.

The slot 62 is formed as a long slot including two side walls. The locking mechanism 63 is disposed on one side wall forming the slot 62. The other side wall forming the slot 62 is a precisely machined flat face with a high hardness, which serves as a position determining reference surface. The slot 62 is adapted to be inserted by the saw blade 400, and the locking mechanism 63 is adapted to press and fix the saw blade 400 against the position determining reference surface after the insertion of the saw blade 400 and thus to snap-fittingly fix the saw blade 400 in the slot 62. The locking mechanism disposed on one side wall of the slot can provide necessary pressure for locking the saw blade that is inserted into the slot, and press the saw blade inserted into the slot against the other side wall of the slot, and its position determining accuracy is ensured by the machining accuracy of the other side wall so that the position of the saw blade can be accurately calculated.

A saw blade limiting block 401 is disposed at an end of the saw blade 400 near the end effector. When inserting the saw blade 400 into the slot 62 of the end tracker 6, the saw blade limiting block 401 provides a limiting function to limit a relative position of the saw blade and the slot along a length direction of the saw blade.

The locking mechanism 63 includes a resilient ball mechanism 631 for providing an elastic force to press and fix the saw blade 400 against the position determining reference surface. The number of the ball mechanisms 631 may be one or more. Preferably, there are two resilient ball mechanisms. When the saw blade 400 has not been inserted into the slot, the resilient ball mechanism can be retracted back from the side wall of the slot. When the saw blade 400 has been inserted into the slot, the resilient ball mechanism extends from the side wall and abuts against the saw blade with a large pressure to fix the saw blade.

Figure 9:
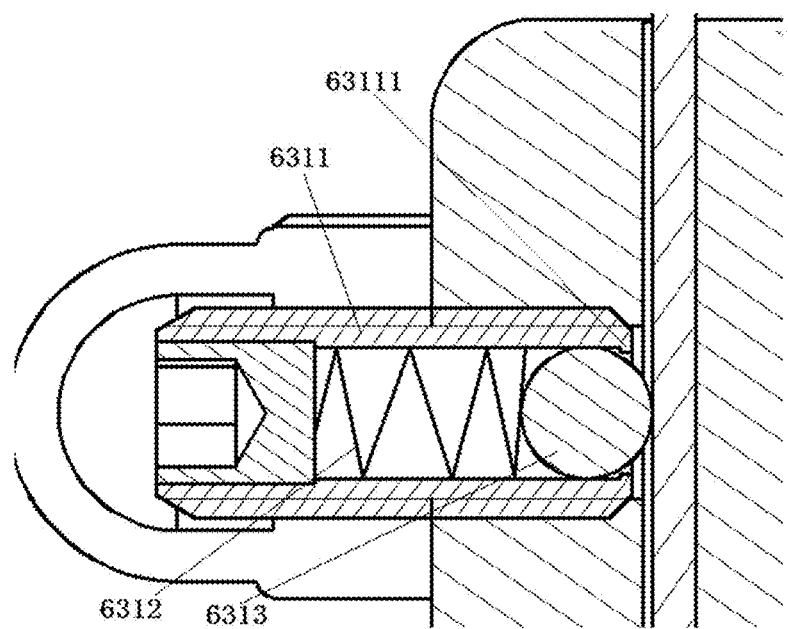
FIG. 9 is a structural schematic diagram of a resilient ball mechanism portion of an end tracker in an embodiment of the disclosure.

As shown in FIG. 9, a structural schematic diagram of a resilient ball mechanism 631 as an embodiment is provided. The resilient ball mechanism 631 includes an accommodating tube 6311, a spring 6312 and a resilient ball 6313; the side wall of the slot 62 on which the locking mechanism is disposed includes a through hole, and the accommodating tube 6311 is fixed in the through hole; one end of the spring 6312 is fixed at a bottom portion of the accommodating tube 6311, and the other end of the spring 6312 is connected to the resilient ball 6313. By the connection of the spring and the resilient ball, a large pressure can be applied for clamping the saw blade. A resilient ball limiting block 63111 is disposed at an end of the accommodating tube 6311 near the resilient ball 6313. The resilient ball limiting block 63111 can limit a position of the resilient ball 6313 in the accommodating tube 6311 to prevent the resilient ball 6313 from leaving the accommodating tube 6311 under the elastic force of the spring.

When the saw blade 400 has not been inserted, the spring 6312 is in a compressed state in the accommodating tube 6311, and the elastic force of the spring 6312 can press the resilient ball 6313 against the side face opposite to the side face on which the through hole is located, i.e., the position determining reference surface, and the resilient ball limiting block 63111 restricts the resilient ball 6313 from leaving the accommodating tube 6311. When the end tracker is being snap-fittingly mounted to the saw blade 400, the slot 62 of the end tracker is aligned to the saw blade 400, and the saw blade 400 is inserted into the slot 62. During the insertion of the saw blade 400 into the slot 62, the spring 6312 is compressed within the accommodating tube due to the elastic force, thereby leaving a gap in the slot 62 so that the saw blade 400 can be inserted into the slot 62. After determining that the saw blade 400 has snap-fittingly mounted into place (i.e., the saw blade 400 abuts against the saw blade limiting block 401 in its length direction, and the saw blade 400 abuts against a long slot bottom face of the slot 62 in its depth direction), the saw blade 400 is firmly pressed against the position determining reference surface of the slot 62 by the coaction of the spring 6312 and ball 6313.

On the other side face of the end tracker main body 61, there are 3-5 reflective balls 7. As shown in FIG. 8, an end reflective ball 71 is disposed at a vertex portion of the end tracker main body 61. The end reflective ball 71 is located close to the end of the saw blade 400 after the end tracker 6 is snap-fittingly mounted to the saw blade 400. In some embodiments, an extension line of a central longitudinal axis of the saw blade 400 passes through a centre of sphere of the end reflective ball 71. Such position of the reflector ball 71 allows tracking the position of the single end reflector ball 71 by using an optical navigation device, which facilitates the accurate position determining of the end of the saw blade 400 and improves the position determining accuracy.

With the above configuration, on one hand, the end tracker 6 has a relative small size suitable for being mounted on the saw blade; and on the other hand, when the end tracker is mounted on the saw blade, the accurate position determining of the end of the saw blade can be ensured by accurate machining and position layout. More importantly, it is very conveniently to use, mount and dismount the end tracker 6. When the end tracker 6 is needed, the saw blade 400 can be easily snap-fittingly mounted into the slot 62 of the end tracker 6 due to the resilient ball mechanism 631; after it is snap-fittingly mounted into place, the optical navigation device 600 can determine the position of the coordinate system in which the end tracker 6 is located by tracking the reflective balls on the end tracker 6, and thus accurately determine the end position of the saw blade 400. When the end tracker 6 is not needed, the end tracker 6 can also be easily disengaged from the saw blade 400.

The steps of the method for positioning and determining the end position of the saw blade 400 by using the end tracker 6 will be described in detail below.

The coordinate system in which the reflective balls on the end tracker 6 are located is defined as $C_V$, since a relative position relationship of the position determining reference surface forming the slot 62 and this coordinate system is known. In use, the saw blade 400 is snap-fittingly mounted into the slot 62 of the end tracker, and a center plane of the saw blade 400 coincides with one of coordinate planes of the coordinate system $C_V$ of the end tracker, so that after the end tracker 6 is snap-fittingly mounted in place, the position of the coordinate system of the reflector balls on the end tracker 6 accurately represents the position of the plane of the saw blade 400. The optical navigation device 600 can determine the position of the coordinate system in which the end tracker is located by tracking the position information of the reflector balls on the end tracker, and accurately determine the position information of the plane of the saw blade, i.e., position information of an end point of the saw blade.

Figure 10:
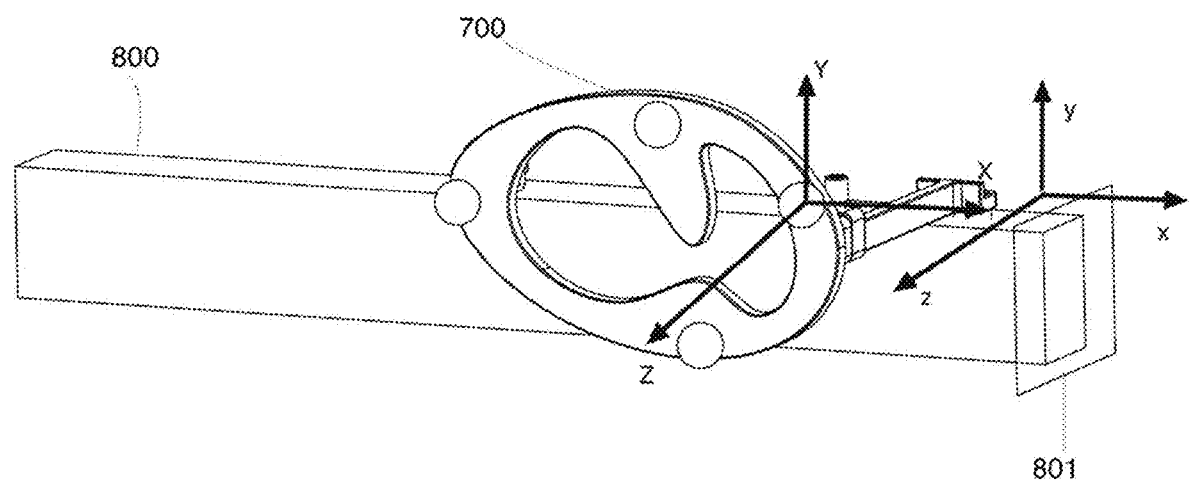
FIG. 10 is a schematic diagram of a position relationship of a reference frame and a plane to be cut in an embodiment of the disclosure.

As shown in FIG. 10, a reference frame (its structure is not shown) is disposed within the system, which is fixedly mounted on a surface of a target object to be cut, also referred to as target reference frame. A rigid connection is formed between the target reference frame and the target object, and a coordinate system in which the reference frame is located is set to be $C_T$. The optical navigation device scans the target object to achieve registration, and by scanning the reference frame, a spatial relative position of the coordinate system in which the reference frame is located and the target object to be cut can be obtained.

A plane to be cut of the object to be cut is set in the host, and a coordinate system in which the plane to be cut is located is set to be $C_P$. Since a relative position of the plane to be cut in the object to be cut is known and the relative position of the object to be cut and the reference frame is known, a spatial relative position relationship $[RT]_{TP}$, of the coordinate system $C_T$ in which the reference frame is located and the coordinate system $C_P$ in which the plane to be cut is located can be determined, wherein $C_T=[RT]_{TP} \ulcorner C_P$, $[RT]_{TP}$ denotes a "rotation translation matrix". Suppose that the coordinate system $C_T$ in which the reference frame is located is first rotated by $\Psi°$ around a Z-axis, then rotated by $\theta°$ around a Y-axis, and finally rotated by $\Phi°$ around the Z-axis, and then translated by "a" along an X-axis, translated by "b" along the Y-axis, and translated by "z" along the Z-axis; and in this way, a unique "rotation translation matrix" $C_T$ can be obtained.

Figure 11:
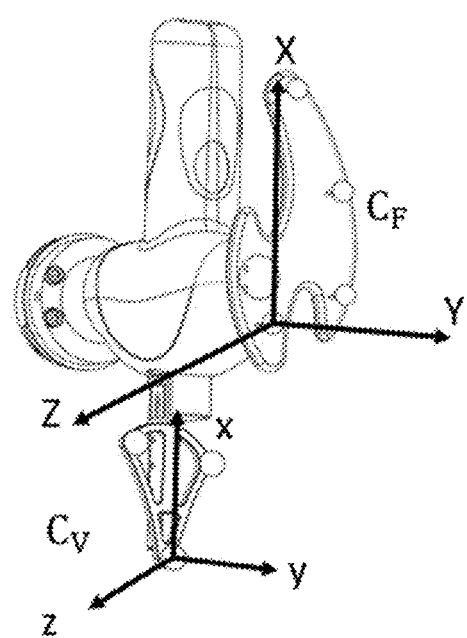
FIG. 11 is a schematic diagram of a position relationship of an end tracker and a main body tracker in an embodiment of the disclosure.
Figure 12:
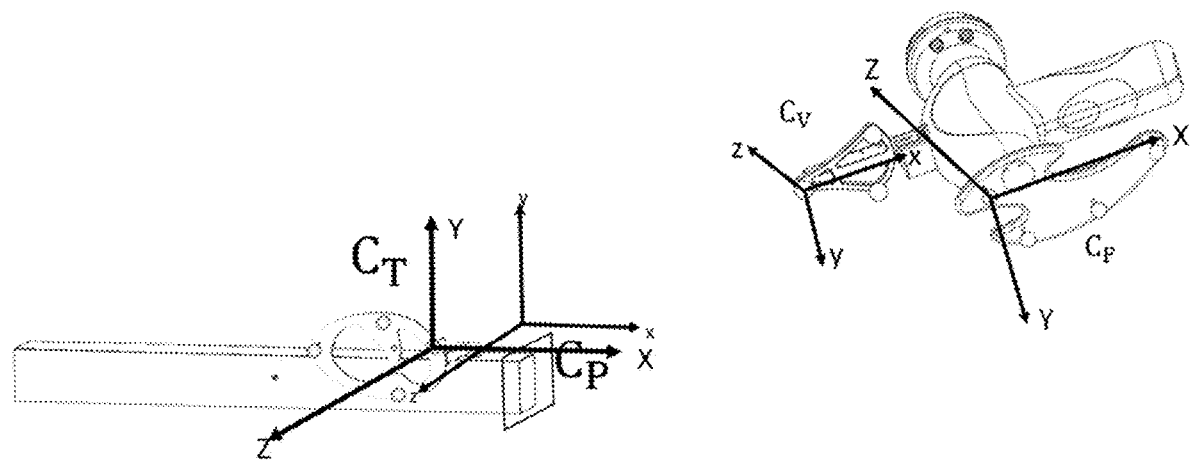
FIG. 12 is a schematic diagram of a position relationship of an end effector and a target to be cut in an embodiment of the disclosure.

As shown in FIG. 11, the coordinate system in which the end tracker 6 is located is set to be $C_V$, and the coordinate system in which the main body tracker 500 is located is set to be $C_F$. A relative position relationship of $C_V$ and $C_F$ is $[RT]_{FV}$. When both the end tracker 6 and the main body tracker 500 are mounted, a relative position relationship $[RT]_{FV}$ of them can be calculated by reading tracking information of them from the optical navigation device 600.

A method of accurately determining the position of the end of the surgical tool in real time by using the accurate position determining device provided in the disclosure includes at least two phases, which, for convenience of description, are a position predetermining phase and a navigating and position determining phase, respectively. When the method steps are described, a term "initial position" used refers to: the collaborative robotic arm has undergone a wide range of movement and is close to the target object to be cut, but still maintains a certain distance from the target object, the distance should at least provide sufficient space to mount and dismount the end tracker 6 as described above. It will be understood that the initial position can be any position close to the target object to be cut and at a certain distance from the target object.

I. Position Predetermining Phase

Figure 13:
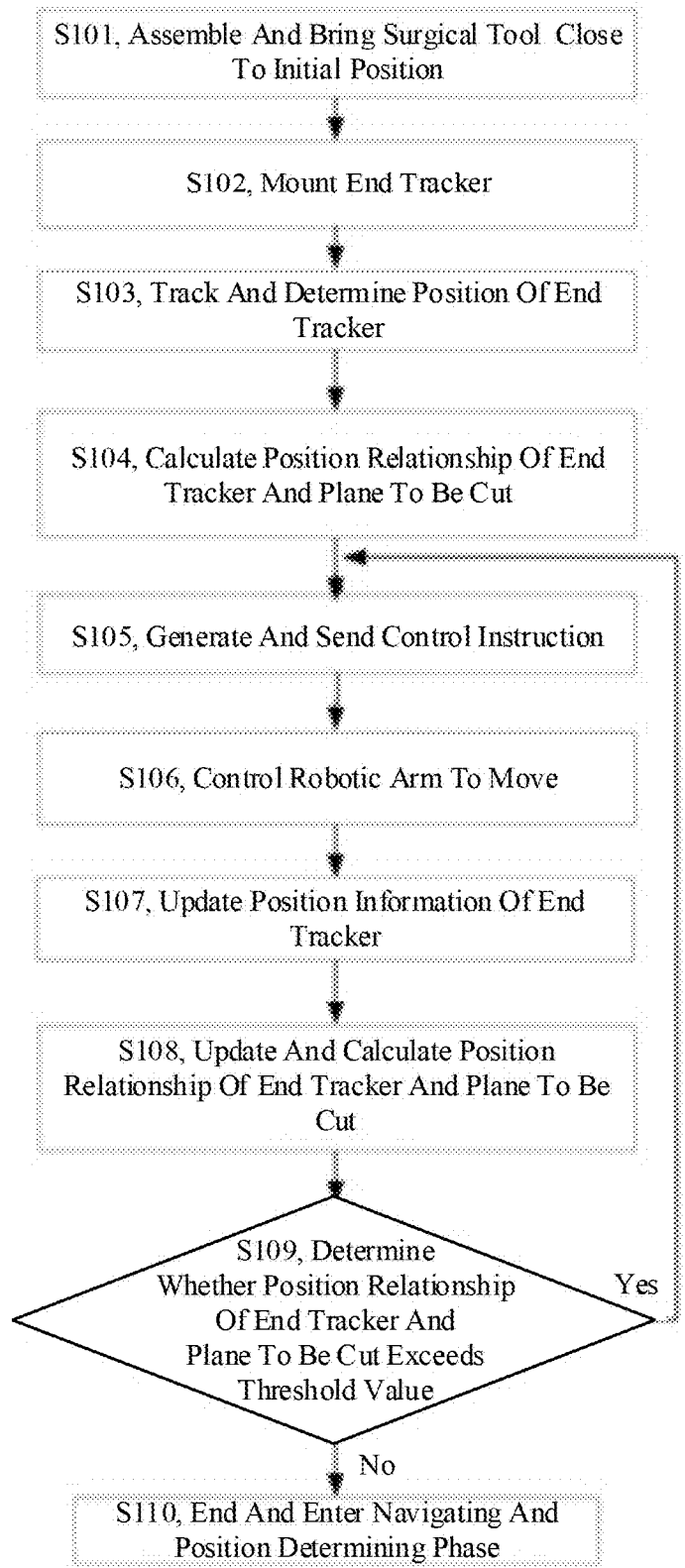
FIG. 13 is a flow diagram of a position predetermining phase of a position determining method in an embodiment of the disclosure.

As shown in FIG. 13, the position predetermining phase includes the following steps.

At Step S101, the surgical tool is assembled and brought close to the initial position. In this step, the end effector 300 is mounted at the end flange 202 of the collaborative robotic arm 200, the saw blade 400 is mounted at a saw blade end of the end effector 300, and the main body tracker 500 is disposed at the end effector 300. The collaborative robotic arm 200 is moved by manually dragging or machine command control, so that the saw blade 400 is brought to a position close to the target to be cut, i.e., arriving at the initial position.

In step S102, the end tracker is mounted. In this step, the end tracker 6 as described above is snap-fittingly mounted to the saw blade 400 to ensure that the saw blade 400 is snap-fittingly mounted in place into the slot 62 of the end tracker 6. In the length direction, one end of the saw blade 400 should abut against the saw blade limiting block 401. In the depth direction, the saw blade 400 should abut against the long slot bottom face of the slot 62.

The person skilled in the art can understand that it is also possible to first snap-fittingly mount the end tracker 6 to the saw blade 400 and then move the collaborative robotic arm 200 so that the saw blade 400 is brought to a position close to the target to be cut, i.e., the initial position. In other words, Steps S101 and S102 are interchangeable in step order.

In Step S103, the end tracker is tracked and positioned. In this step, the optical navigation device tracks the positions of the reflective balls on the end tracker 6 and calculates the position information of the coordinate system in which the end tracker 6 is located.

In Step S104, a position relationship of the end tracker and the plane to be cut is calculated. In this step, the host portion processes the position information obtained by the optical navigation device and calculates a position relationship of the coordinate system in which the end tracker is located and the coordinate system in which the plane to be cut is located.

Specifically, the optical navigation device can observe both the end tracker 6 for the saw blade and the target reference frame, and as described above, the coordinate system in which the end tracker is located is $C_V$, and the coordinate system in which the target reference frame is located is $C_T$, and a relative position relationship $[RT]_{VT}$ of them can be calculated based on the pose information of them obtained by the optical navigation device.

Suppose that a position relationship of the coordinate system $C_V$ in which the end tracker 6 is located and the coordinate system $C_P$ in which the plane to be cut is located is set to be $[RT]_{VP}$, and $[RT]_{VP}$ can be obtained by the following calculation:

$$\because C_V = [RT]_{VP} \cdot C_P$$

$$\therefore [RT]_{VP} = C_V \cdot C_P^{-1}$$

$$\because C_T = [RT]_{TP} \cdot C_P$$

$$\therefore [RT]_{TP}^{-1} \cdot C_T = C_P$$

$$\therefore [RT]_{VP} = C_V \cdot ([RT]_{TP}^{-1} \cdot C_T)^{-1}$$

In other words, the position relationship $[RT]_{VP}$ of the coordinate system $C_V$ in which the end tracker 6 is located and the coordinate system $C_P$ in which the plane to be cut is located can be obtained according to the coordinate system $C_V$ in which the end tracker 6 is located, the coordinate system $C_T$ in which the reference frame is located, and the known position relationship of the reference frame and the plane to be cut.

In Step S105, a control instruction is generated and sent to the control unit. In this step, according to $[RT]_{VP}$ obtained by the calculation in Step 104, the control instruction for controlling a movement route of the robotic arm is generated and sent to the control unit.

In Step S106, the robotic arm is controlled to move according to the instruction. In this step, the robotic arm moves according to the instruction.

Ideally, in Step S106, after the collaborative robotic arm completes the movement according to the instruction, the coordinate system $C_V$ in which the end tracker 6 is located and the coordinate system $C_P$ in which the plane to be cut is located can coincide exactly. Then, $[RT]_{VP}$ is a fourth-order identity matrix E, and the end of the saw blade is accurately aligned with the position of the plane to be cut.

However, due to errors caused by the design of the control system of the robotic arm or the like, it is actually difficult for the robotic arm 200 to move accurately according to the route planned by the instruction. Therefore, after Step S106, the end position of the surgical tool usually does not accurately reach the position of the plane to be cut. Therefore, the following steps are also included:

In Step S107, tracking position information of the end tracker 6 is updated. In this step, after the robotic arm 200 completes movement according to the control instruction in Step S106, the optical navigation device continues to track the positions of the reflective balls on the end tracker 6 and calculates the position information of the coordinate system in which the end tracker 6 is located to obtain the updated position information.

In Step S108, the position relationship of the end tracker and the plane to be cut is updated and calculated. In this step, according to the updated position information of the end tracker 6, a new position relationship $[RT]_{VP}'$ of the coordinate system $C_V$ in which the current end tracker 6 is located and the coordinate system $C_P$ in which the plane to be cut is located is calculated and updated;

In Step S109, it is determined whether the position relationship of the end tracker and the plane to be cut exceeds a threshold value. In this step, a difference between the new position relationship $[RT]_{VP}'$ and the fourth-order identity matrix E is calculated, and the difference of them is compared with a predetermined threshold value to determine whether the difference exceeds the threshold range.

If the determining result in Step S109 is that the difference exceeds the threshold range, as shown in FIG. 13, the method returns to Step S105 to generate and send a control instruction to the control unit. It is different for the Step S105 at this time in that the control instruction for controlling the movement route of the robotic arm is generated according to $[RT]_{VP}'$ calculated in Step S108 and sent to the control unit. In Step S106, the robotic arm is controlled to complete the movement according to the instruction. After the movement, the method proceeds with Step S107 to Step S109.

In Step S110, if the determining result in Step S109 is that the difference is less than the threshold range, the system considers the end of the surgical tool has moved in place, generates and sends an instruction for stopping the movement; the position predetermining phase ends, and it is ready to proceed with the navigating and position determining phase.

In this way, on one hand, by tracking the position of the end tracker, it is possible to achieve more accurate position determining of the end position of the saw blade; on the other hand, according to the position relationship of the coordinate system in which the tracked saw blade end is located and the coordinate system in which the target cutting plane is located, the instruction for controlling the movement of the robotic arm is generated to control the robotic arm to complete the movement, so that the robotic arm can move to close to the desired target position; furthermore, after each movement of the robotic arm, the position relationship of the tracked saw blade end and the target cutting plane is updated, and if the robotic arm has not moved to the desired target position or if the movement error is large, the robotic arm is controlled to move again; and such process is a convergence process, which can be repeated in this way, and it is possible to approach the desired target position by successive approximation and achieve accurate alignment when the position predetermining phase ends.

Figure 14:
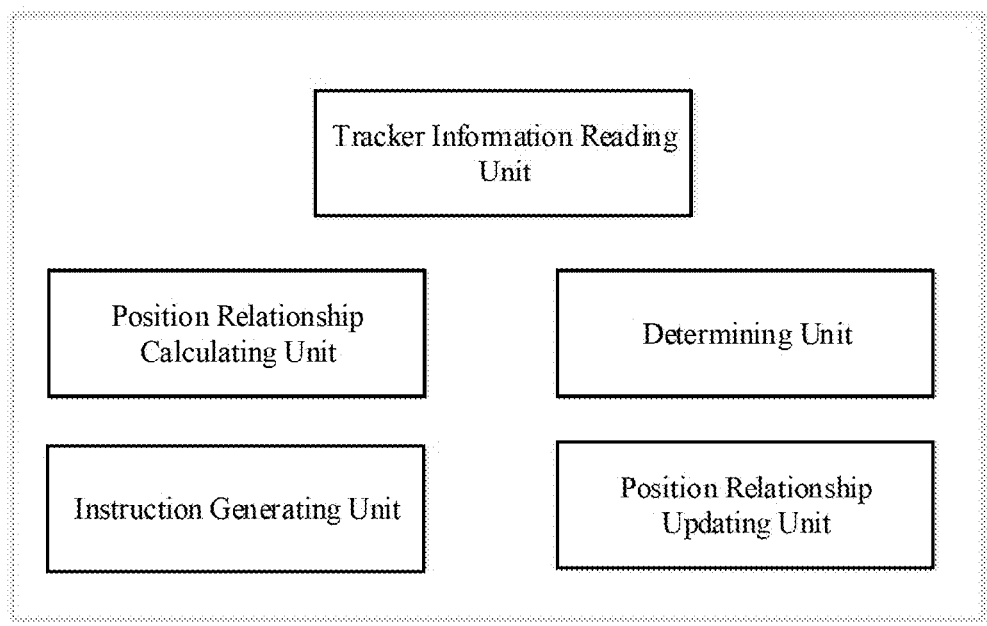
FIG. 14 is a schematic diagram of unit modules for implementing steps of a position determining method according to an embodiment of the disclosure.

To perform the above steps, as shown in FIG. 14, the disclosure designs the host and control system by providing following units:

- a tracker information reading unit, including a unit for reading information of the end tracker which reads the coordinate system $C_V$ in which the end tracker 6 is located from the optical navigation device, and a unit for reading information of the reference frame, which reads the coordinate system $C_T$ in which the reference frame is located from the optical navigation device;
- a position relationship calculating unit, for calculating the position relationship $[RT]_{VP}$ of the coordinate system $C_V$ in which the end tracker is located and the coordinate system $C_P$ in which the plane to be cut is located, based on the coordinate system $C_V$ in which the end tracker 6 is located and the coordinate system $C_T$ in which the reference frame is located;
- an instruction generating unit for generating and sending the control instruction for controlling the movement of the robotic arm based on the position relationship calculated by the position relationship calculating unit;
- a position relationship updating unit for updating and calculating the position relationship $[RT]_{VP}'$ of the coordinate system $C_V$ in which the end tracker is located and the coordinate system $C_P$ in which the plane to be cut is located after the robotic arm moves by $[RT]_{VP}$; and
- a determining unit for determining whether $[RT]_{VP}'$ is less than the predetermined threshold value; if it is greater than the predetermined threshold value, generating and sending the control instruction to control the movement of the robotic arm according to the position relationship $[RT]_{VP}'$ updated and calculated by the position relationship updating unit; and if it is less than the predetermined threshold value, generating the instruction to stop the movement.

II. Navigating and Position Determining Phase

After the position predetermining is finished, the system proceeds with the navigating and position determining phase.

Figure 15:
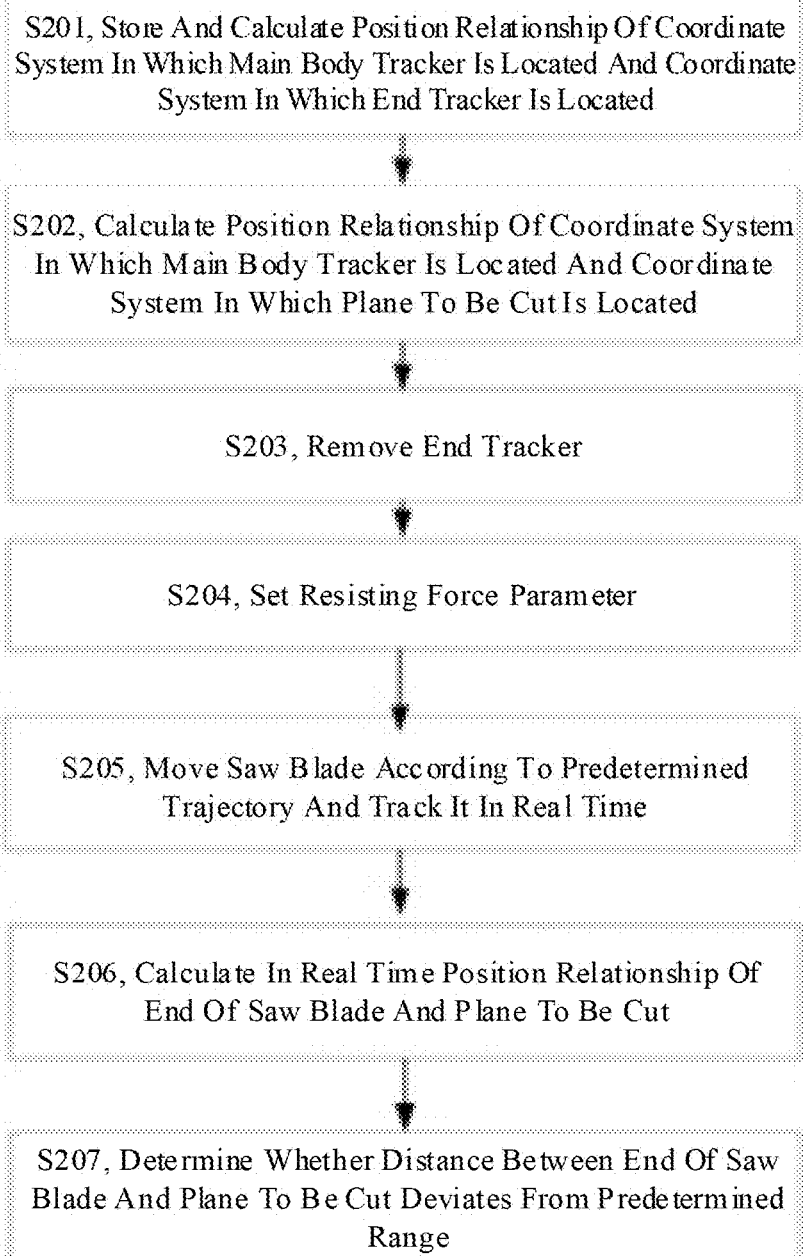
FIG. 15 is a flow diagram of a navigating and position determining phase of a position determining method in an embodiment of the disclosure.

As shown in FIG. 15, the navigating and position determining phase includes the following steps.

In Step 201, a position relationship of the coordinate system in which the main body tracker is located and the coordinate system in which the end tracker is located is calculated and stored. After the position predetermining phase is finished, based on the position information of the coordinate system $C_F$ in which the main body tracker 500 is located and the coordinate system $C_V$ in which the end tracker 6 is located obtained from the tracking of the optical navigation device 600, the relative position relationship of $C_V$ and $C_F$ is calculated as $[RT]_{FV}$, and $[RT]_{FV}$ is stored as a first calibration parameter.

In Step 202, a position relationship of the coordinate system in which the main body tracker is located and the coordinate system in which the plane to be cut is located is calculated according to the first calibration parameter. Herein, the relationship $[RT]_{FP}$ between the coordinate system $C_F$ in which the main body tracker 500 is located and the coordinate system $C_P$ in which the plane to be cut is located is calculated according to following formulas and stored as a second calibration parameter:

$$\because [RT]_{FP} = [RT]_{FV} \cdot [RT]_{VP}$$

$$\because [RT]_{VP} = C_V{}^{-1}([RT]_{TP}{}^{-1} \cdot C_T)^{-1}$$

$$\therefore [RT]_{FP} = [RT]_{FV} \cdot C_V{}^{-1}([RT]_{TP}{}^{-1} \cdot C_T)^{-1}$$

In Step S203, the end tracker 6 that is snap-fittingly mounted on the end of the saw blade is removed.

In Step S204, a resisting force parameter is set. In this step, the resisting force parameter of the collaborative robotic arm 200 during its movement is set. The resisting force along a direction in a plane same as the plane in which the saw blade 400 is located can be set to be 0, and the resisting force along a direction perpendicular to the plane in which the saw blade 400 is located is set to be F=kx, wherein a resisting force coefficient k is 4000-6000 N/mm, preferably 5000 N/mm, x is a moving distance, and F is the resisting force. By setting the resisting force, it is ensured that along the direction perpendicular to the plane in which the saw blade 400 is located, a larger force needs to be applied to move the saw blade, so that a range of movement of the collaborative robotic arm 200 is limited and controlled so that it is moved within the plane to be cut, which can prevent errors caused when the saw blade deviates from the target plane due to uttering or misoperation of the saw blade.

Step S205 is a step of controlling the saw blade to move according to a predetermined trajectory and tracking in real time.

The host portion issues an instruction to make the collaborative robotic arm 200 drive the saw blade 400 to move according to the predetermined trajectory, and during the movement of the saw blade, the optical navigation device 600 tracks and reads the position information of the coordinate system in which the main body tracker 500 is located in real time, and calculates a real time position of the end of the saw blade 400 according to the second calibration parameter $[RT]_{FP}$.

In Step S206, a position relationship of the coordinate system in which the end point of the saw blade is located and the coordinate system in which the plane to be cut is calculated in real time. According to the coordinate system $C_T$ in which the reference frame of the target to be cut is located, and the known position relationship of the coordinate system in which the reference frame is located and the coordinate system in which the plane to be cut is located, the coordinate system $C_P$ in which the plane to be cut can be determined, i.e., the position relationship of a plane position of the end of the saw blade 400 and the coordinate system $C_P$ in which the plane to be cut is located can be calculated in real time.

In Step S207, it is determined whether a distance between the end of the saw blade and the plane to be cut deviates from a predetermined range and an alarm is issued. In this step, if it is determined that the distance between the end of the saw blade and the plane to be cut deviates from the predetermined range, the alarm is issued in various ways such as sound and color display to prompt the operator to intervene and adjust, or the system automatically makes a response adjustment, until all cutting operations within the plane to be cut are completed.

Figure 16:
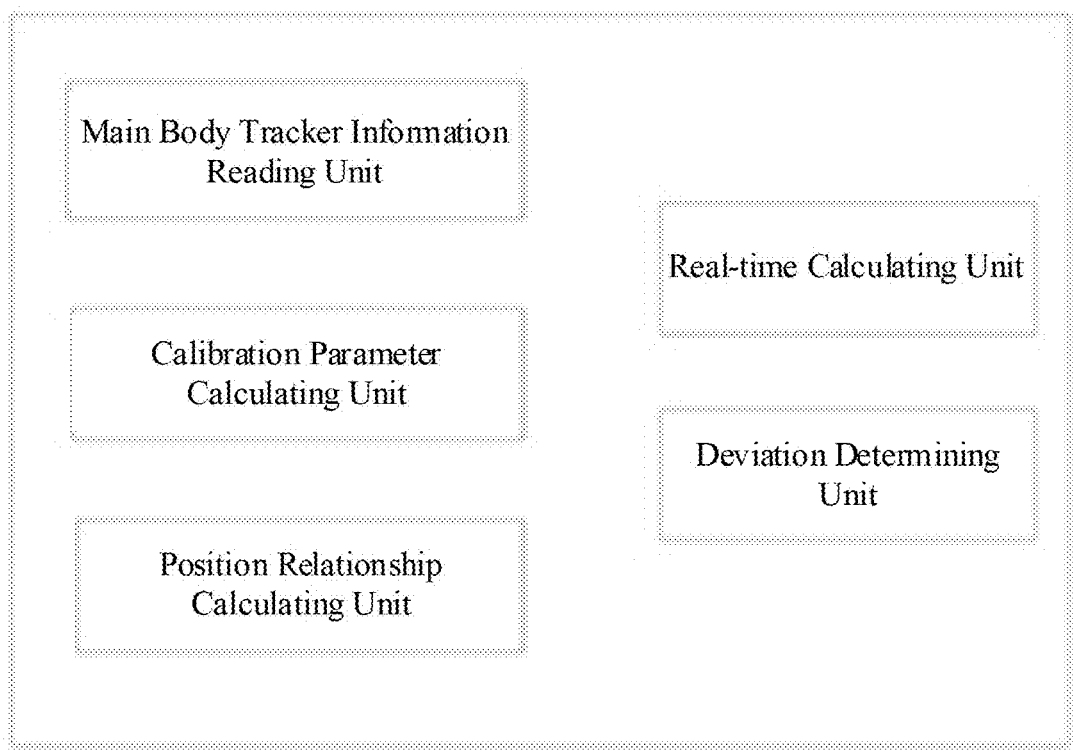
FIG. 16 is a schematic diagram of unit modules for implementing navigating and position determining steps of a position determining method in an embodiment of the disclosure.

To perform the above steps, as shown in FIG. 16, the disclosure designs the host and control system by providing following units:

a main body tracker information reading unit for reading from the optical navigation device the position information of the coordinate system in which the main body tracker 500 is located;

a calibration parameter calculating unit for calculating the position relationship $[RT]_{FV}$ of the coordinate system $C_V$ and the coordinate system $C_F$ based on the coordinate system $C_V$ in which the end tracker 6 is located and the coordinate system $C_F$ in which the main body tracker 500 is located;

a position relationship calculating unit for calculating the position relationship $[RT]_{FP}$ between the coordinate system $C_F$ in which the main body tracker 500 is located and the coordinate system $C_P$ in which the plane to be cut is located, based on the position information of the coordinate system in which the main body tracker 500 is located, the position information of the coordinate system $C_T$ in which the reference frame is located, the calibration parameter $[RT]_{FV}$, and the known position relationship of the coordinate system in which the reference frame is located and the coordinate system in which the plane to be cut is located;

a real-time calculating unit for calculating and obtaining the real-time position of the end of the surgical tool according to the position information of the coordinate system in which the main body tracker 500 is located and the position relationship $[RT]_{FP}$ that are real-time obtained; and a deviation determining unit for calculating the distance between the plane position of the end of the surgical tool and the coordinate system in which the plane to be cut is located, and determining whether the distance deviates from the predetermined range.

Figure 17:
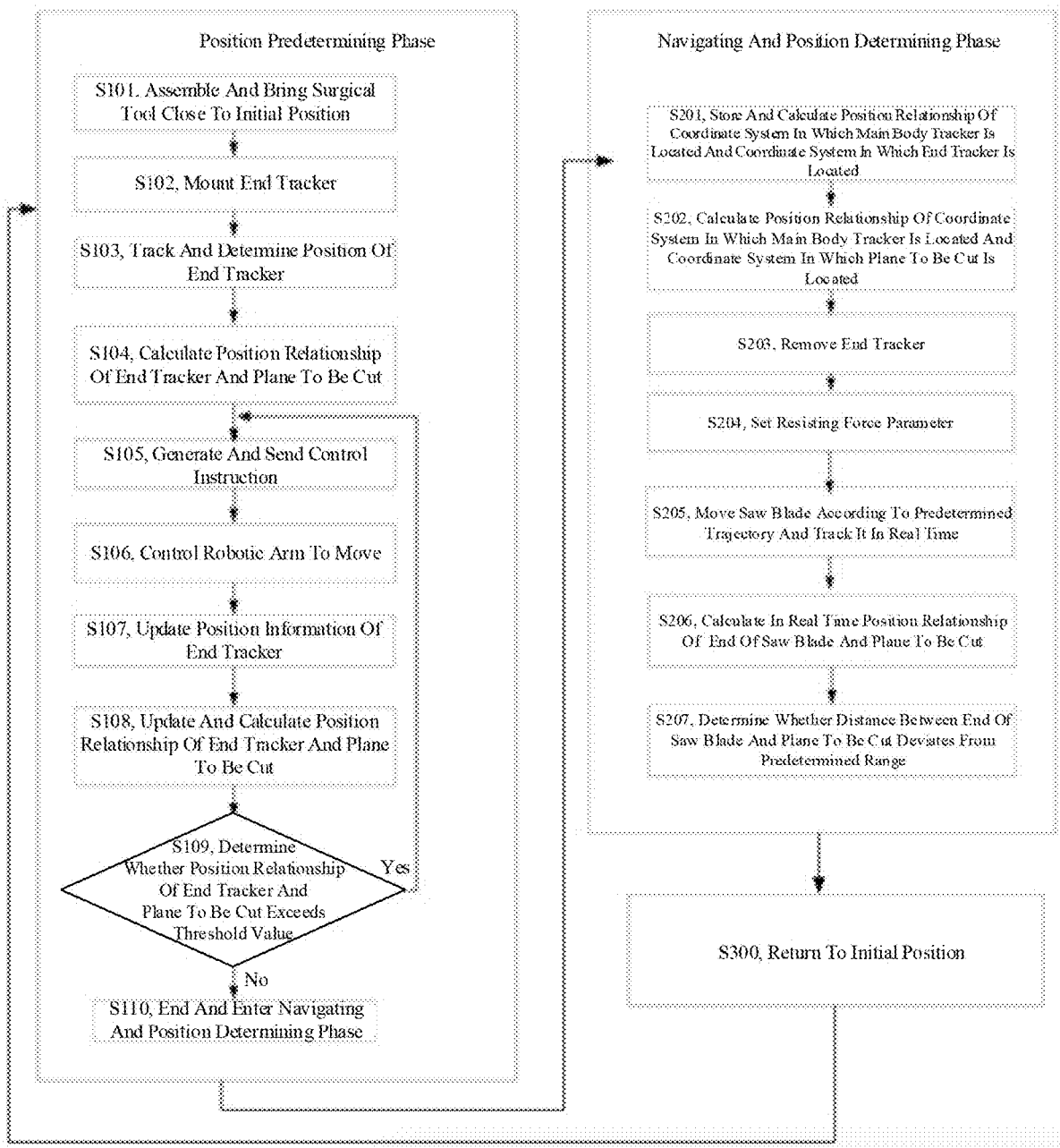
FIG. 17 is a flow diagram of a method in an embodiment of the disclosure when applied to a scenario with multiple planes to be cut.

For scenarios involving multiple planes to be cut, as shown in FIG. 17, after the navigating and position determining phase is finished, i.e., after the surgical tool has completed operations at a plane to be cut for this embodiment, the method provided by the disclosure also includes Step S300: controlling the end of the surgical tool to return to the initial position. In this step, the robotic arm 200 is controlled by the control unit to move such that the saw blade 400 is returned to a position at a certain distance from the target to be cut. For example, it can be the initial position of the previous position predetermining phase, or a position different from the initial position of the previous position predetermining phase, as long as the position is relatively close to the target object to be cut and at a certain safety distance from the target object.

After Step S300, the end tracker 6 is snap-fittingly mounted on the saw blade 400 once again, i.e., the method returns to Step 102 of the position predetermining phase and continues to perform the steps of the position predetermining phase and the navigating and position determining phase as described above, until cutting operations at a second plane to be cut have been completed. Herein, in Steps S104, S108, S202, and S206, the position relationship is calculated by using the coordinate system in which the second plane to be cut is located.

After the cutting operations at the second plane to be cut have been finished, the system determines whether there is a third plane to be cut, and if so, continues to perform the Step S300 and repeats the above steps, until operations at all planes to be cut have been completed.

For example, in a total knee replacement surgery, multiple planes need to be cut, generally at least five different cutting planes. In this case, the embodiment provides a solution in which after cutting operations of a plane to be cut have been finished, the surgical tool returns to the initial position and performs the position-predetermining, navigating and position determining steps again with respect to a next plane to be cut, so as to ensure that it can be accurately positioned and navigated for each plane to be cut. Compared with existing technologies, the solution according to the embodiment performs accurate position predetermining each time before performing cutting operations with respect to a target plane to be cut, and records the calibration parameters after the position predetermining and proceeds with the navigating and position determining, which can eliminate position determining errors generated during each movement process of the surgical tool, enable the whole position determining process to be more precise and provide a high accuracy. Furthermore, since the solution according to the embodiment is accomplished based on real-time calculation of the position relationships of the surgical tool, the end effector and the target to be cut, the accurate position determining with respect to each plane to be cut can be ensured while it will not take too much time, which takes into account both speed and accuracy of the position determining.

In the embodiment, there is also provided a storage medium having a program stored thereon, wherein a device in which the storage medium is located is controlled to carry out the above method when the program is executed.

In the embodiment, there is also provided a processor including a program of the processor, wherein a device in which the processor is located is controlled to carry out the above method when the program is executed. It should to be noted that although the disclosure takes a collaborative robotic arm as an example in the embodiments, it will be clearly understood by a person skilled in the art that the apparatus, method and system according to the disclosure can also be applied to a non-collaborative robotic arm, i.e. a robotic arm operated entirely by a control unit.

The device embodiments as described above are merely illustrative, wherein the units described as discrete components may or may not be physically separated, and a component shown as a unit may or may not be a physical unit, i.e., it may be located at a place or can be distributed among multiple network units. Some or all of the modules can be selected according to actual needs to achieve the objectives of the solutions of the embodiments. Those of ordinary skill in the art can understand and implement it without creative work.

The above embodiments are only used to illustrate the technical solutions of the disclosure, rather than limiting them; although the disclosure has been described in detail with reference to the above embodiments, those of ordinary skill in the art should understand that: the described technical solutions according to the above embodiments may be modified, or some of the technical features may be equivalently replaced; and these modifications or replacements do not cause the essence of the corresponding technical solutions to deviate from the spirit and scope of the technical solutions of the embodiments of the disclosure.

What is claimed is:

1. A system for determining an end position of a surgical tool, comprising: an optical navigation device and a robotic arm device, wherein an end effector is connected to an end of the robotic arm device, a main body tracker is disposed at a main body of the end effector, a surgical tool is disposed at an end of the end effector, an end tracker is disposed at the surgical tool, and the end tracker is detachably mounted at a distal end of the surgical tool.

2. The system according to claim 1, wherein the end tracker comprises a tracker main body, a slot, a locking mechanism and a plurality of reflective balls, wherein the slot and the locking mechanism are located on one side face of the tracker main body, the reflective balls are located on the other side face of the tracker main body.

3. The system according to claim 2, wherein the locking mechanism is located on one side wall forming the slot, the slot is adapted to be inserted by the surgical tool and to snap-fittingly fix the surgical tool by means of the locking mechanism.

4. The system according to claim 3, wherein the locking mechanism comprises a resilient ball mechanism for providing an elastic force for fixing the surgical tool against the other side wall of the slot.

5. The system according to claim 4, wherein the resilient ball mechanism comprises an accommodating tube, a spring and a resilient ball, the side wall of the slot on which the locking mechanism is disposed comprises a through hole, the accommodating tube is fixed in the through hole, one end of the spring is fixed at a bottom portion of the accommodating tube, and the other end of the spring is connected to the resilient ball.

6. A surgical tool accurate position determining method using a system, the method comprising a position predetermining phase and a navigating and position determining phase, wherein in the position predetermining phase, an optical navigation device is used to track an end tracker to determine a position of a distal end of a surgical tool; and in the navigating and position determining phase, the optical navigation device is used to track a main body tracker to determine the position of the distal end of the surgical tool, and wherein the system comprises the optical navigation device and a robotic arm device, an end effector is connected to an end of the robotic arm device, the main body tracker is disposed at a main body of the end effector, the surgical tool is disposed at an end of the end effector, the end tracker is disposed at the surgical tool, and the end tracker is detachably mounted at the distal end of the surgical tool.

7. The surgical tool accurate position determining method according to claim 6, wherein in the position predetermining phase, the optical navigation device tracks a position of the end tracker, calculates a position relationship of the end tracker and a plane to be cut, and controls a movement of the robotic arm device.

8. The surgical tool accurate position determining method according to claim 7, wherein before the optical navigation device tracks the position of the end tracker, the method further comprises a step of assembling the surgical tool and bringing it close to an initial position, and mounting the end tracker.

9. The surgical tool accurate position determining method according to claim 7, wherein a control instruction for controlling the movement of the robotic arm device is generated based on the calculated position relationship of the end tracker and the plane to be cut.

10. The surgical tool accurate position determining method according to claim 6, wherein after the robotic arm device has moved according to the instruction, the method further comprises a step of updating and calculating position information of the end tracker.

11. The surgical tool accurate position determining method according to claim 10, wherein the step of updating and calculating the position information of the end tracker comprises a step of updating tracking position information of the end tracker and a step of updating and calculating the position relationship of the end tracker and the plane to be cut.

12. The surgical tool accurate position determining method according to claim 10, wherein the method further comprises: a step of determining whether a distance between the end tracker and the plane to be cut exceeds a threshold range, in which step, if the distance exceeds the threshold range, a control instruction is generated and sent to a control unit according to the updated and calculated position relationship to control the robotic arm device to move according to the instruction.

13. The surgical tool accurate position determining method according to claim 6, wherein in the navigating and position determining phase, the optical navigation device tracks a position of the main body tracker, calculates a position relationship of the distal end of the surgical tool and the plane to be cut, and controls the movement of the robotic arm device.

14. The surgical tool accurate position determining method according to claim 13, wherein before the navigating and position determining phase, the method further comprises a step of calculating a position relationship of the end tracker and the main body tracker and a step of storing the position relationship as a first calibration parameter,
wherein the method further comprises: a step of calculating a position relationship of the main body tracker and the plane to be cut according to the first calibration parameter, and a step of storing the position relationship as a second calibration parameter,
wherein during navigation, a real time position of the distal end of the surgical tool is calculated and obtained according to the second calibration parameter.

15. The surgical tool accurate position determining method according to claim 6, wherein the navigating and position determining phase comprises following steps:
a step of calculating and storing a position relationship of a coordinate system in which the main body tracker is located and a coordinate system in which the end tracker is located;
a step of calculating and storing a position relationship of the coordinate system in which the main body tracker is located and a coordinate system in which a plane to be cut is located;
a step of removing the end tracker, controlling the surgical tool to move according to a predetermined trajectory, and also tracking position information of the main body tracker; and
a step of calculating, in real time, a distance between an end point position of the surgical tool and the plane to be cut according to the tracked position information of the main body tracker.

16. A surgical system for driving and determining a position of a surgical tool, comprising:
an end effector for connecting to the surgical tool;
a robotic arm device connected to the end effector;
a main body tracker disposed at the end effector;
an end tracker for detachably connecting to the surgical tool, wherein there is a predetermined position relationship between the end tracker and the surgical tool;
an optical navigation device for obtaining a position information between the main body tracker and the end tracker; and
a controller for controlling the robotic arm device, wherein the controller is configured to obtain in a first phase a position information of the surgical tool according to a position information of the end tracker obtained by the optical navigation device and obtain in a second phase the position information of the surgical tool according to a position information of the main body tracker obtained by the optical navigation device.

17. The surgical system according to claim 16, wherein the end tracker is configured to be stayed on the surgical tool in the first phase.

18. The surgical system according to claim 16, wherein the controller is configured to calculate a relative position relationship between the end tracker and the main body tracker according to the position information of the end tracker and the position information of the main body tracker which have not been obtained in the first phase.

19. The surgical system according to claim 18, wherein the controller is configured to, when obtaining in the second phase the position information of the surgical tool according to the position information of the main body tracker obtained by the optical navigation device, obtain the position information of the surgical tool according to the position information of the main body tracker and the relative position relationship.

20. The system according to claim 1, wherein the distal end of the surgical tool is an end of the surgical tool farther away from a robotic arm operator and closer to a patient.

\* \* \* \* \*